United States Patent [19]

Davis

[11] 4,249,899
[45] Feb. 10, 1981

[54] WARM WATER DENTAL SYRINGE

[75] Inventor: Eugene B. Davis, Newberg, Oreg.

[73] Assignee: A-Dec, Inc., Newberg, Oreg.

[21] Appl. No.: 12,148

[22] Filed: Feb. 14, 1979

[51] Int. Cl.³ .............................................. A61G 17/02
[52] U.S. Cl. ..................................... 433/32; 433/80;
 128/224; 222/146 HE
[58] Field of Search ....................... 32/22; 433/32, 80;
 128/224, 239, 400; 222/146 HE

[56] References Cited

U.S. PATENT DOCUMENTS

| 795,056 | 7/1905 | Noah | 128/224 |
|---|---|---|---|
| 1,313,861 | 8/1919 | Reid et al. | 32/22 |
| 1,837,932 | 12/1931 | Weigle | 128/224 |
| 1,958,332 | 5/1934 | Carpenter | 32/22 |
| 2,227,566 | 1/1941 | Angell | 32/22 |
| 3,254,646 | 6/1966 | Staunt et al. | 128/224 |
| 3,393,676 | 7/1968 | Kummer et al. | 32/22 |
| 3,698,088 | 10/1972 | Austin, Jr. | 32/22 |
| 3,831,815 | 8/1974 | Glasgow | 32/70 |

Primary Examiner—Gene Mancene
Assistant Examiner—John J. Wilson
Attorney, Agent, or Firm—Klarquist, Sparkman, Campbell, Leigh, Hall & Whinston

[57] ABSTRACT

The specification discloses a dental syringe with a tubular handle adapted to pre-heat water before it is delivered through the syringe tip into a patient's mouth. Water and air supply hoses are connected to the handle, and electric heater and thermostat elements are mounted within the handle for maintaining the temperature of the water therein at from about 95° F. to about 105° F.

1 Claim, 6 Drawing Figures

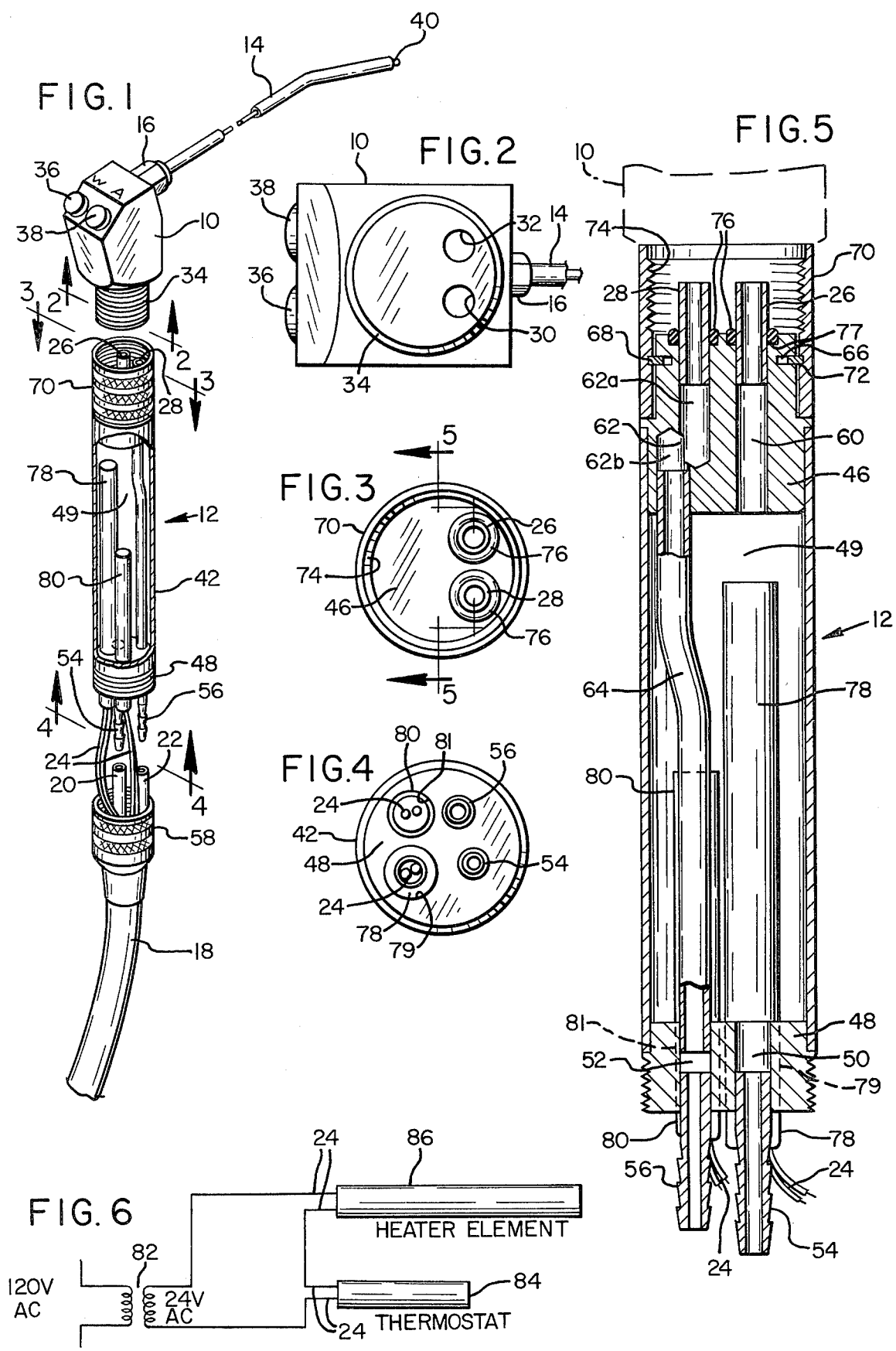

WARM WATER DENTAL SYRINGE

BACKGROUND OF THE INVENTION

The present invention relates to dental syringes, and more particularly to a dental syringe with a handle adapted to pre-heat water from a supply hose before it is delivered through the syringe tip into a patient's mouth.

Dental syringes are widely used by dentists, dental hygenists, dental assistants and the like. They are hand-held instruments which deliver water and air into a patient's mouth for washing and drying purposes. One such dental syringe is disclosed in U.S. Pat. No. 3,698,088. It includes a head, a handle coupled to the head, an elongate discharge tip, and a coupling for mounting the tip on the head. Supply hoses for air and water extend through the handle and are connected to the head. Valves in the head are selectively hand operated to discharge water, air, or both through the distal end of the tip.

Patient comfort is a very important objective in modern dentistry. The delivery of cold water into a patient's mouth during treatment can be discomforting when the patient's teeth or gums are sensitive to sudden changes in temperature. This is especially so when, for example, a hygenist is scaling plaque off of the teeth below the gum line. Even when local or general anesthetic has been used, e.g. during the performance of certain dental surgical operations such as a root canal, exposed tissues and nerve endings may be subjected to thermal shock if washed with cold water.

Therefore it is desirable to pre-heat the water before it is delivered into the patient's mouth. However, the water must not be too hot or similar undesirable effects will result. Lukewarm water at or near body temperature is preferred.

Heretofore, a number of apparatus have been developed for supplying warm water through a dental syringe. One apparatus included a remote water reservoir or tank, a heater element in the tank, a thermostat for regulating the temperature of the water in the tank, and a pump for pumping water from the tank through a water supply hose to a dental syringe. However, the water supply hose must be at least several feet in length in order for the syringe to be easily manipulated. The water cools while in the hose. Since the syringe is operated to deliver water intermittently, water frequently stands in the supply hose. The longer it stands, the more it cools. This problem has been alleviated somewhat by continuously recirculating the water, however such a design has necessitated the use of an additional water supply hose. In addition, it has been difficult to regulate the temperature of the water delivered with this design. The temperature fluctuates depending upon the length of the water supply hose and the amount of heat dissipated therefrom.

Another apparatus included a heater wire which runs the length of the water supply hose. The heater wire must either be mounted externally of the hose or embedded therein during the extrusion of the hose. High production cost has been a principal drawback of this design.

Yet another apparatus included an electric heater element in the head of the dental syringe which keeps the head warm. The shortcoming of this design is that only the initial squirt of water discharged from the syringe is warm, having stood in the head a sufficient length of time to be pre-heated to the desired temperature.

SUMMARY OF THE INVENTION

It is an object of the present invention to provide a dental syringe adapted to pre-heat water from a supply hose before it is delivered through the syringe tip into a patient's mouth.

It is another object of the present invention to provide a dental syringe handle including a water chamber having heater and thermostat elements mounted therein.

It is yet another object of the present invention to provide a warm water dental syringe which will discharge water at a temperature of from about 95° F. to about 105° F.

It is still another object of the present invention to provide a dental syringe adapted to pre-heat air from a supply hose before it is delivered through the syringe tip into a patient's mouth.

The present invention provides a warm water dental syringe including a head, a tip extending from the head, and handle means extending from the head. The head has a water passage therethrough which communicates with a water passage through the tip. The handle means includes a water chamber which communicates with the water passage through the head. An electric heater element heats water in the chamber. The handle means further includes connecting means for attaching a water supply hose so that water can flow therefrom into the chamber.

BRIEF DESCRIPTION OF THE DRAWINGS

FIG. 1 is an exploded view of a warm water dental syringe forming one embodiment of the present invention with parts broken away;

FIG. 2 is an enlarged elevational view of the head of the dental syringe of FIG. 1 taken along line 2—2 of FIG. 1;

FIG. 3 is an enlarged elevational view of the handle of the dental syringe of FIG. 1 taken along line 3—3 of FIG. 1;

FIG. 4 is an enlarged elevational view of the handle of the dental syringe of FIG. 1 taken along line 4—4 of FIG. 1;

FIG. 5 is an enlarged sectional view of the handle of the dental syringe of FIG. 1 taken along line 5—5 of FIG. 3; and FIG. 6 is a schematic diagram of an electric circuit which accomplishes the desired regulation of the temperature of the water within the handle of the dental syringe of FIG. 1.

DESCRIPTION OF THE PREFERRED EMBODIMENT

Referring to FIG. 1, the illustrated embodiment of a warm water dental syringe constructed in accordance with the present invention includes a head 10, a handle 12 coupled to the head, and elongate tip 14, and a coupling 16 for mounting the tip on the head. A flexible tube 18 encloses a water supply hose 20, an air supply hose 22, and electric wires 24 which are connected to the lower end of the handle 12.

Water and air are supplied from the hoses 20 and 22, through the handle 12 in which the water is heated, to water and air connector pipes 26 and 28 at the upper end of the handle as will be described. The connector pipes 26 and 28 are inserted into water and air passages 30 and 32 (FIG. 2) in an externally threaded shank 34 (FIG. 1) at the bottom of the head 10. The water and air passages 30 and 32 extend from the end of the shank 34 through the head 10 to an internally threaded cylindrical cavity (not shown) in the top frontal surfaces of the head in which the coupling 16 is suitably secured as, for example, in the manner shown in co-pending application Ser. No. 974,366.

The tip 14 (FIG. 1) comprises inner and outer elongate, co-axial spaced apart pipes which define water and air passages which communicate with the water and air passages 30 and 32 respectively through the head 10 in the manner also described in co-pending application Ser. No. 974,366. Push buttons 36 and 38 on the top rear surface of the head 10 are coupled to suitable, normally closed valves (not shown) mounted in the water and air passages 30 and 32 so as to be selectively handoperated in order to discharge water, air, or both through the distal end 40 of the tip 14.

Referring to FIG. 1, the handle 12 includes an outer elongate cylindrical tube 42 adapted to be grasped by the user's hand. The tube 42 has upper and lower ends in the form of cylindrical plugs 46 and 48 (FIG. 5) which fit tightly into the ends of the tube. The interior bore of the tube between the plugs 46 and 48 defines a water chamber 49. Sealant such as solder may be applied to the plugs to ensure a leak-proof water chamber. The tube 42 is preferably formed from brass tubing having an inside diameter of nearly three-quarters of an inch. The length of the water chamber 49 is approximately three and five-eighths inches. The volume of the water chamber is large enough, after subtracting the volume of the hereafter described elements mounted therein, to allow numerous successive squirts of heated water to be discharged through the tip.

As shown in FIG. 5, the lower plug is provided with connecting means for attaching the water and air supply hoses 20 and 22. Side-by-side water and air passages 50 and 52 extend through the lower plug 48. Tubular water and air supply barbs 54 and 56 are tightly fit into the lower ends of the water and air passages 50 and 52 respectively. The water and air supply hoses 20 and 22 are tightly fit over the supply barbs 54 and 56 respectively (FIG. 1). The lower portion of the plug 48 is externally threaded and an internally threaded ring 58 attached to the hose 18 is screwed over the plug 48 to shield the supply hose and electric wire connections.

The upper plug 46 (FIG. 5) is provided with coupling means for releasably securing the upper end of the handle 12 to the shank 34 of the head 10. Side-by-side water and air passages 60 and 62 extend through the upper plug 46. The air passage 62 is formed by drilling slightly offset upper and lower holes 62a and 62b partially into opposite ends of the plug 46 so that they meet. The water and air connector pipes 26 and 28 are tightly fit into the upper ends of the water and air passages 60 and 62 respectively. The upper and lower ends of an air conduit pipe 64 inside the water chamber 49 are tightly fit into the air passages 62 and 52 respectively. The pipe 64 has a bend in its intermediate portion so that it clears the casing of the thermostat later described. Air from the supply hose 22 can thus be delivered directly through the handle 12 to the syringe head 10. Heat from the water inside the chamber is conducted through the pipe 64 and warms the air therein.

The upper portion of the upper plug 46 has an annular groove 66 in its outer periphery. A conventional slip ring 68 having a segment missing from its body is expanded and slid over the upper plug 46 until it seats in the groove 66. Thereafter a tubular sleeve 70 having an annular groove 71 in its inner surface is slid over the upper plug 46 and the slip ring 68 by slightly compressing the slip ring. When the slip ring 68 seats in the groove 72 in the sleeve it slightly expands to lock the sleeve in position about the upper plug 46. The sleeve 70 has internal threads 74 adapted to be threadedly engaged with the external threads on the shank 34 of the head 10.

The handle 12 and the shank 34 must be aligned so that the connector pipes 26 and 28 (FIGS. 1, 3 and 5) will be received in the passages 30 and 32 (FIG. 2) in the shank. Elastomeric O-rings 76 (FIGS. 3 and 5) surround the connector pipes 26 and 28 and are seated in annular cavities 77 formed in the plug 46. The O-rings 76 are squeezed between the upper plug 46 and the shank 34 to provide water and air seals.

Referring to FIGS. 1, 4 and 5, an electric heater element of the resistance type is mounted inside an elongate cylindrical casing 78 mounted within the water chamber 49. The lower end of the casing 78 is tightly fit into and extends through a mounting hole 79 (shown in phantom lines in FIG. 5) which extends through the lower plug 48 on the side thereof opposite from the water passage 50. Preferably the casing 78 is formed from copper tubing and extends axially within the tube 42 over substantially the entire length of the water chamber 49 so that the water within the chamber can be heated more uniformly.

An electrical thermostat of the bi-metal type is mounted inside an elongate cylindrical casing 80 (FIGS. 1, 4 and 5) also mounted within the water chamber 49. The casing 80 is also preferably formed from copper tubing. The lower end of the casing 80 is tightly fit into and extends through a mounting hole 81 (shown in phantom lines in FIG. 5) which extends through the lower plug 48 on the side thereof opposite from the air passage 52. The casing 80 is spaced from the casing 78 so that the thermostat contained therein will monitor the water temperature within the chamber 49 rather than the temperature of the casing 78. The electric wires 24 are connected to the heater and thermostat elements within the casing 78 and 80 and extend from the lower ends of the casings.

FIG. 6 shows an example of a simple electric circuit for the warm water dental syringe of the present invention which will accomplish the desired regulation of the temperature of the water within the chamber 49. A 120 volt AC electric power source is connected to the primary leads of a transformer 82 which steps the voltage down to 24 volts. A bi-metal thermostat 84 (inside the casing 80) and a heater element 86 (inside the casing 78) are connected in series to the secondary winding of the transformer 82.

In operation, when the heater element 86 is energized it heats the water within the chamber 49 until the water has been heated to the upper temperature limit of the thermostat 84. At this time the thermostat 84, which functions as a temperature sensitive switch, opens. The heater element 86 is de-energized and the water within the chamber 49 cools until the lower temperature limit of the thermostat 84 is reached. At this time the thermostat 84 closes, energizing the heater element 86 which heats the water within the chamber 49 until the upper temperature limit of the thermostat 84 is once again reached. In this manner, the temperature of the water within the chamber 49 is regulated so that it is always between the upper and lower temperature limits of the thermostat.

It is preferred to deliver water through the dental syringe at body temperature, i.e. 98.6° F. However, due to the nature of the circuit, the temperature of the water within the chamber must necessarily fluctuate above and below this desired temperature. It is preferable to use a thermostat element with upper and lower temperature limits near 98.6° F. However, thermostats which can detect very small variations in temperature are typically more expensive. Therefore, it is acceptable to use a thermostat element which will maintain the temperature of the water within the chamber at from about 95° F. to about 105° F.

From the foregoing, it will be apparent that the invention permits of modification in arrangement and detail. For example, the tip and the handle can be integrally formed to the head. The tube 42 defining the water chamber 49 can have a layer of thermal insulation material. Various types of thermostats may be used, e.g. one made of a material having a negative coefficient of resistance. However, such adaptations and modifications, as well as others, are within the spirit and scope of the present invention.

I claim:

1. A warm water dental syringe comprising:

a head having a water passage and an air passage therethrough;

a tip extending from the head and having a water passage therethrough communicating with the water passage through the head, and an air passage therethrough communicating with the air passage through the head;

an elongate tube adapted to be grasped as a handle and defining in its interior a water chamber, the tube having upper and lower ends;

a plug in each of said ends closing the same and defining with the inner wall of said tube said water chamber, each plug having water and air passages therethrough;

coupling means for releasably securing the upper end of the tube to the head so that the water passage through the upper end of the tube communicates with the water passage through the head and so that the air passage through the upper end of the tube communicates with the air passage through the head;

an air conduit mounted in the chamber and extending between and communicating with the air passages in said upper and lower plugs;

connecting means for attaching a water supply hose and an air supply hose at the lower end of the tube so that water can flow into the chamber through the water passage through the lower end of the tube and air can flow into the air conduit through the air passage through the lower end of the tube;

a first elongate cylindrical casing mounted within the water chamber and extending substantially the entire length thereof;

an electric heater element mounted in said first elongate cylindrical casing for heating the water in said chamber;

a second elongate cylindrical casing mounted within the water chamber and spaced from the first casing;

an electric thermostat mounted in said second elongate cylindrical casing for controlling the heater element to regulate the temperature of the water in the chamber;

said first and second casings extending through said lower mounting plug whereby said heater element and said thermostat may be easily replaced.

* * * * *